(12) United States Patent
Nordvik

(10) Patent No.: US 6,273,868 B1
(45) Date of Patent: Aug. 14, 2001

(54) BREAST PUMP

(75) Inventor: Tone Nordvik, Oslo (NO)

(73) Assignee: Mamma Lactans AS, Oslo (NO)

( * ) Notice: Subject to any disclaimer, the term of this patent is extended or adjusted under 35 U.S.C. 154(b) by 0 days.

(21) Appl. No.: 09/308,290

(22) PCT Filed: Nov. 7, 1997

(86) PCT No.: PCT/NO97/00293

§ 371 Date: Jul. 12, 1999

§ 102(e) Date: Jul. 12, 1999

(87) PCT Pub. No.: WO98/22160

PCT Pub. Date: May 28, 1998

(30) Foreign Application Priority Data

Nov. 12, 1996 (NO) .......................................... 964791
Sep. 29, 1997 (NO) .......................................... 974492

(51) Int. Cl.$^7$ ........................................... A61M 1/06
(52) U.S. Cl. ............................................... 604/74
(58) Field of Search ..................... 604/317, 327, 604/346, 540, 73, 74, 75, 76; 119/14.01, 14.02, 14.2, 14.24, 14.25, 14.29, 14.3–14.31, 14.38–14.39, 14.4–14.44

(56) References Cited

U.S. PATENT DOCUMENTS 5,049,126 * 9/1991 Larsson ................................. 604/74

FOREIGN PATENT DOCUMENTS

1745262 * 7/1992 (SU) .

* cited by examiner

Primary Examiner—Glenn K. Dawson
Assistant Examiner—Catherine Serke
(74) Attorney, Agent, or Firm—Browdy & Neimark

(57) ABSTRACT

Apparatus for milking a human breast comprising a breast cup, collecting means connected to the breast cup, a vacuum source, at least one source of pressurized fluid, and a regulating device. The breast cup includes a generally conical portion and a generally cylindrical portion connected to the part is the conical portion which is smallest in diameter The breast cup includes first and second stimulating members for stimulating the nipple and an area of the breast, respectively.

8 Claims, 4 Drawing Sheets

BREAST PUMP

CROSS-REFERENCE TO RELATED APPLICATION

The present application is the national stage under 35 U.S.C. 371 of PCT/NO97/00293, filed Nov. 7, 1997.

FIELD OF THE INVENTION

The present application relates to a human breast milking apparatus which simulates a suckling infant comprising a breast cup, a collecting means, a vacuum source, and a regulating means.

BACKGROUND OF THE INVENTION

In recent years the number of women who breast-feed their infants has increased steadily. It is considered to be best for both mother and child from a nutritious and a psychological point of view.

The most usual way in which to give an infant mother's milk is to let the infant suck directly from the breast. However, there are a number of cases where it is not appropriate or possible to allow the infant to suck straight from the breast. Examples of such cases may be:

when the infant is premature and unable to suck, when the mother has insufficient milk, when the mother is ill and needs stronger stimulus, medically indicated mastitis where the mother cannot give milk to the infant due to the treatment, and where the breast must be depleted of milk.

For purely practical reasons it may also be desirable to enable persons other than the mother to feed the infant.

There are a number of physiological and psychological factors which affect milk production, and which can arrest it. An essential factor is the stimulation of the breast to initiate milk production. The stimulation of the breast comprises a total of three components which must be present if milk production is to commence:

Stimulation of the breast itself, where the greatest stimulus is at the edge of the areola. There lie the so-called "milk lakes", which, when subjected to pressure, release oxytocin from the pituitary gland. This hormone has a direct impact on the lactiferous ducts so that these are expanded and opened for depletion. This happens when the infant grasps around the breast by opening its mouth wide. The jaw and the lips will then stimulate the areola, which is about 2.5 to 3 cm from the base of the nipple.

Stimulation of the actual nipple, wherein it is squeezed and massaged. This happens in that the infant's tongue and palate encircle the nipple. Tactile stimulation results in a strong stimulus and thus a hormonal response.

The actual sucking which takes place when the infant sucks.

A number of different breast cups and associated breast pumps have been developed which to some degree simulate some of the aforementioned factors.

In addition to having to be capable of simulating these factors, the breast pumps must also be comfortable to use, they must be soft and adaptable to different shapes and sizes of breasts. At the same time, they must be easy to use.

A number of different breast pumps are known which consist of a cup or similar device, which is placed over the breast, a manual or mechanical vacuum pump connected to the cup which generates an intermittent vacuum in the cup, and a receptacle for the expressed milk. The expressed milk flows typically from the body and into a receiving container for storage and later use.

U.S. Pat. No. 5,049,126 discloses an insert for a breast cup or hood for a breast pump, the object of which is to achieve a more realistic simulation of an infant pressing and massaging the nipple. The insert consists of a funnel-shaped portion in the form of a truncated cone with a tubular portion provided at that part of the funnel-shaped portion which is smallest in diameter. In the tubular portion there is provided at least one elongated opening located at a point overlying the nipple when the apparatus is in use. This elongated opening in the tubular portion is provided with a flexible membrane. When a negative pressure is created in the insert with the aid of a vacuum pump, the flexible membrane will be drawn into the insert and will gently squeeze and massage the nipple to enhance the production of milk. This insert will not stimulate the rest of the breast or the area around the nipple. According to the description, the actual funnel-shaped portion seems to be made of a rigid material, so that it may be difficult to adapt the insert to different breast shapes and sizes. Since the insert is rigid, this could cause some discomfort to the user. In addition, the insert is intended to be put into the breast cup of an already existing breast pump.

U.S. Pat. No. 4,680,028 discloses a breast cup or receptor for a breast pump, which breast cup is made of a transparent, flexible material, for example, silicone rubber. The breast cup is in the form of a funnel-shaped portion having a tubular extension. In the transition area between the funnel-shaped portion and the tubular portion, the wall thickness is reduced with a view to massaging the nipple and the surrounding area as a result of the suction effect which is produced by a vacuum pump. There is also a reduction in the thickness of the wall in an area of the funnel-shaped portion having largest diameter, permitting the fingers of the mother to massage the underlying other parts of the breast.

EP-198 469 describes a breast pump, including a vacuum pump. The breast cup of this apparatus consists of parts which are to simulate the mouth, throat and jaw of an infant. The breast cup grips around the breast by means of pressure generated by the pump. An aperture valve controls the pressure. During use, the woman can massage her breast and control the rhythm.

WO-92/07593 describes an elastomeric liner or insert for a breast cup of a breast pump, which insert has recesses and grooves to enable it to be better adapted to the breast. The insert consists of a funnel-shaped portion in the form of a truncated cone and a tubular portion which is connected to that part of the funnel-shaped portion which is smallest in diameter. On the outside of the funnel-shaped portion there are arranged arcuate, oval recesses to provide a thin membrane in the insert at the area around the nipple. According to the description, the purpose of this is to prolong the duration of suction effect produced by the pump stroke, so that the milk production increases and that the insert is softer and more comfortable to the user. This insert will not be capable of giving the desired stimulus to the nipple or to the rest of the breast. In addition, according to the description, this insert is intended to be placed into an already existing breast cup of a breast pump.

U.S. Pat. No. 4,964,851 discloses an electrically-powered breast pump, consisting of a breast cup of a partly flexible plastic material, a suction pump and a rotatable valve. The rotatable valve directs the suction from the pump in alternating fashion between the breast cup and the receiving container, so that there is a reciprocal suction action on the breast.

EP 727 234 discloses an insert for a funnel-shaped breast cup. The insert is provided with portions of reduced thickness to enable these portions to move towards the inside of the funnel-shaped breast cup and in this way give some stimulation to the aerola region when a vacuum is generated in the breast cup. However, the vacuum and the frequency which provide this stimulation cannot be adjusted independent of one another and it will therefore not be possible to produce a "pulsating wave" from the breast towards the nipple. It may therefore be difficult to achieve the desired degree of stimulation and a large vacuum can at worst cause an obstructive squeezing against the lactiferous ducts, thereby preventing expression of milk.

A major disadvantage with the solutions described above is the lack of stimulation of the area of the breast at and beyond the areola. Most of the solutions described above stimulate only the nipple and the area of the breast immediately around the nipple. Stimulation of this kind is not sufficient to instigate satisfactory milk production. The area of the breast, the areola, which is about 2.5 to 3 cm from the base of the nipple contains a number of so-called "milk lakes" which, when stimulated, will open the lactiferous glands. It is this area which is stimulated by the infant's lips during breast-feeding and which gives a hormonal response in the form of oxytocin. A second disadvantage with several of the apparatus discussed above is that they are made of partly rather inflexible materials which are not sufficiently capable of adapting to the shape of the breast. This could cause the user some discomfort.

SUMMARY OF THE INVENTION

One object of the present invention is therefore to provide a breast cup which to a great degree simulates a suckling infant.

A second object of the invention is to provide an apparatus which makes it possible to stimulate the breast so that strong, stable milk production is rapidly achieved, as is a swift depletion of milk from the breast.

Another object of the invention is to provide an apparatus which does not cause the user any discomfort or irritation.

This is achieved with a human breast milking apparatus including a breast cup, a collecting means connected to the breast cup, a source of vacuum, at least one source of pressurized fluid and a regulating device, which breast cup includes a generally conical portion and a generally cylindrical portion connected to that part of the conical portion.
Amended Sheet
Which is smallest in diameter, characterized in that the breast cup in combination comprises:

a) a first stimulating member for stimulating a nipple, which first stimulating area consists of the generally cylindrical portion (3);
b) a second stimulating member for stimulating an area of the breast immediately around or in the immediate vicinity of the nipple, which second stimulating member is provided at or in the vicinity of that part of the conical portion (2) which is smallest in diameter, which second stimulating member consists of an annular chamber (4) in the wall of the conical portion (2) of the breast cup (1); and
c) a third stimulating member for stimulating an area of the breast 2.5 to 3 cm from the base of the nipple, which third stimulating member (6) consists of a part of the conical portion (2) which is 2.5 to 3 cm from the connection between the cylindrical portion (3) and the conical portion (2), which third stimulating member consists of an annular chamber in the wall of the conical body (2), preferably a chamber in the form of one or more rows of cells (6) interconnected by passages (7), said first stimulating member, which consists of the generally cylindrical portion (3), is connected to a vacuum source having adjustable pressure and frequency, and the second stimulating member is connected to a pressure source, preferably compressed air, having adjustable pressure and frequency, the frequency of the vacuum source and the pressure source being independently adjustable relative to one another, The second stimulating member and the third stimulating member are preferably connected to one or more pressure sources, preferably compressed air, having adjustable pressure and frequency.

The breast cup is preferably made of a flexible, skin-friendly material, preferably silicone.
Amended Sheet The pressure of the first stimulating member can preferably be adjusted within the range of 50 to 220 mm Hg and the frequency can preferably be adjusted within the range of 60 to 120 per minute.

The invention will be explained in more detail below by means of exemplary embodiments with reference to the appended drawings.

DETAILED DESCRIPTION OF THE INVENTION

FIGS. 1 to 4 show different embodiments of breast cups for use in the human breast milking apparatus according to the invention.

The breast cup 1 for use in the human breast milking apparatus of the invention consists of a generally conical portion 2 and a generally cylindrical portion 3 located at that part of the conical portion 2 which is smallest in diameter. The cylindrical portion 3 is tubular and is intended to accommodate the nipple when the breast cup is placed on the breast. The generally conical portion 2 is intended to rest against the actual breast when the breast cup is placed on the breast.

The breast cup 1 has three stimulating members for stimulating the nipple. The first stimulating member consists of a generally cylindrical portion 3. This first stimulating member is approximately the same for all the different embodiments of the breast cup shown in the figures. This first stimulating member stimulates the nipple in that the member is connected to a vacuum source having either pulsating, adjustable pressure or static pressure. This will be explained in more detail below.

Figure 1:
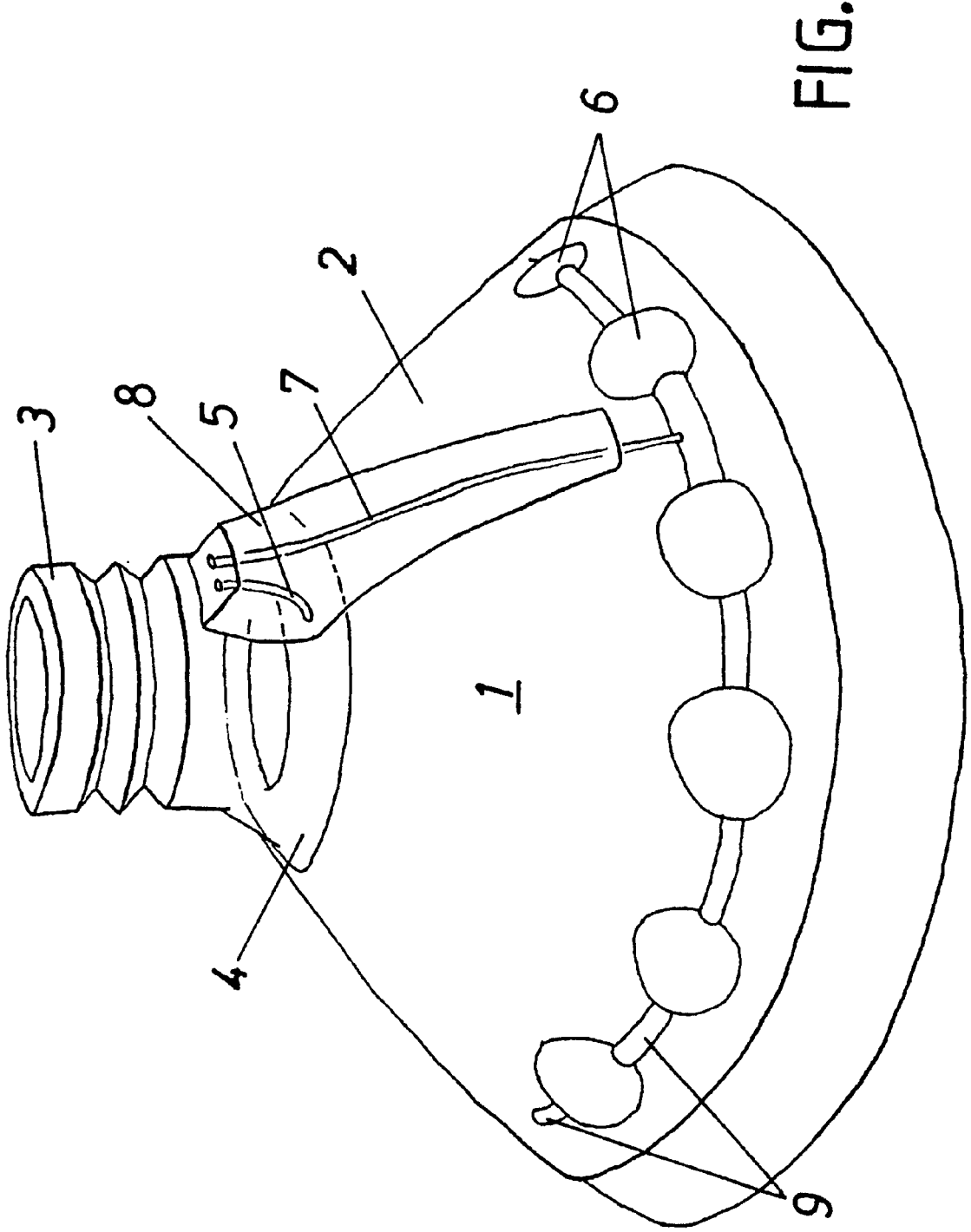
FIG. 1 is a perspective view of a first embodiment of a breast cup for a human breast milking apparatus according to the invention.

The purpose of the second stimulating member is to stimulate the base of the nipple by squeezing and pressing on the area immediately at the base of the nipple. In FIG. 1 this second stimulating member consists of an annular chamber 4 having a supply tube 5 for pressurized fluid. The tube 5 is preferably connected to a pressurized fluid supply via a connecting part 8, which produces either constant or pulsating pressure.

The purpose of the third stimulating member is to stimulate an area further up on the breast about 2.5 to 3 cm from the base of the nipple. As previously mentioned this area is known as the areola and in this area the so-called "milk lakes" are found, which on stimulation will release oxytocin. In FIG. 1 this third stimulating member consists of cells or chambers 6 connected to one another by passages 9. This third stimulating member is connected to a pressurized fluid supply by a supply tube 7 and a connecting part 8.

The cells or chambers 6, the chamber 4 and the passages 7 and 9 are made in the wall of the breast cup 1, so that these areas will have a reduced wall thickness compared to the rest of the breast cup. This means that these areas will be more flexible than the rest of the breast cup.

When using the breast cup according to the first embodiment of the present invention, at least two stimulation areas of the breast will be established which correspond to the stimulation that takes place when an infant is breast-fed. These stimulations are generated by supplying pressure pulses on at least two stimulation areas. The intensity (pressure) and the frequency of these pressure pulses are adjustable so that the user herself can find the rate and intensity best suited to her.

The first stimulation takes place directly on the nipple itself, in that this is squeezed and massaged by an applied vacuum. This stimulation corresponds to the sucking of an infant. The second stimulation takes place in the area immediately adjacent to the nipple, in the areola area, in that this area is squeezed and massaged. This corresponds to the stimulation from the tongue and palate of an infant.

The optional third stimulation takes place in an area about 2.5 to 3 cm from the base of the nipple, in that this area is squeezed and massaged in a manner corresponding to the lips of a nursing infant.

The breast cup illustrated in FIG. 1 is used as follows:

The cylindrical part 3 of the breast cup is connected to a vacuum pump and a milk receiving container by means of a suitable connector (not shown). This part of the apparatus is to stimulate the nipple and this takes place by applying vacuum in the form of pulses. The purpose of this pulsating vacuum is to extract milk from the breast. The vacuum pump should be capable of providing an oscillating pressure and the pump must therefore be equipped with regulating devices, so that the pressure can be adjusted within the range of 50 to 200 mm Hg and the frequency within the range of 60 to 120 per minute.

The first chamber 4 of the breast cup is connected via outlet 5 and an appropriate connector (not shown) to a pressure pump. The pressure pump must be capable of producing an oscillating pressure, and both the pressure and the frequency should be adjustable. This second stimulating member will stimulate the area at the base of the nipple and produce a pulsating compression of this area. By virtue of the fact that the chamber 4 is supplied with pressurized fluid, preferably compressed air, in pulses, the chamber 4 will expand, i.e., it will be inflated, and press against this area. When the pressure is relieved, the chamber 4 will contract, thereby no longer pressing on this area.

The second chamber 6 of the breast cup is connected via the outlet 8 and an appropriate connector (not shown) to a pressure pump. This pressure pump may be the same pressure pump as that connected to the first chamber 4, or it may be a separate pump. In this case too, the pressure and the frequency must be capable of being adjusted by the user, preferably independent of the adjustment of the pressure and frequency in the first chamber 4.

This third stimulating member will stimulate the part of the breast which is about 2.5 to 3 cm from the base of the nipple. By supplying pressurized fluid, preferably compressed air, to the other chambers or cells 6, these will be inflated in the same way as chamber 4, and press on this part of the breast. When the pressure is relieved again, the chamber will contract and no longer press on this area.

The supply of pressurized fluid and vacuum to the three stimulation areas takes place in such manner that a pulsating "wave" is produced from the area furthest from the nipple towards the nipple.

To be able to achieve an independent adjustment of pressure and frequency to all three stimulation areas, there are stringent requirements with respect to the vacuum and pressure pump or pumps and the regulating mechanisms therefor. For example, a combined pressure and vacuum pump may be used. This pump can be provided with a suitable valve member (not shown) which provides the desired pressure and frequency control. One conceivable option is the use of one or two pressure pumps and one vacuum pump which operate independently of one another.

Figure 2:
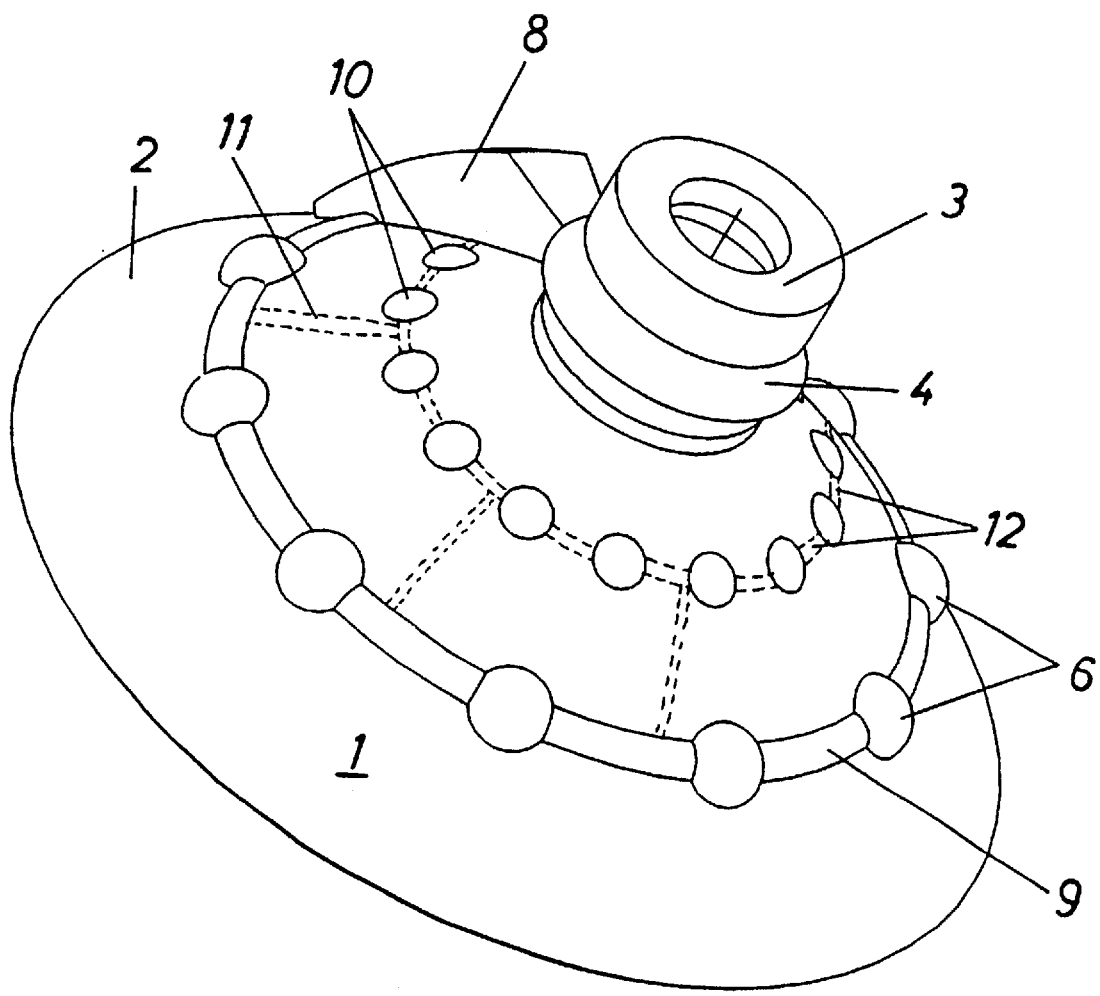
FIG. 2 shows a breast cup according to a second embodiment of the invention.

FIG. 2 shows a second embodiment of the breast cup according to the invention, where the same elements as in the embodiment in FIG. 1 are indicated by means of the same reference numerals. What distinguishes this embodiment from that illustrated in FIG. 1 is that instead of only one row of "cells" as indicated at 6 in FIG. 1, according to this embodiment there are provided at least two rows of "cells" 6 and 10, which decrease in volume in the direction of the generally cylindrical portion 3. The purpose of this is that a wave motion is to be generated from the largest cell towards the smallest, so that the breast is subjected to a wave motion. The cells 10 are interconnected by means of passages 12, and are connected to the first row of cells 6 via passages 11. Optionally, the rows of cells 6 and 10 may have separate supplies of pressurized fluid, to allow the intensity and frequency of the pressurized fluid supply to the cells 6 and 10 to be adjusted independent of one another.

As a variant of the embodiments in FIGS. 1 and 2, the rows of cells 6 and 12 may be replaced by circumferential channels, which would have the same function as the cells 6 and 12.

Figure 3:
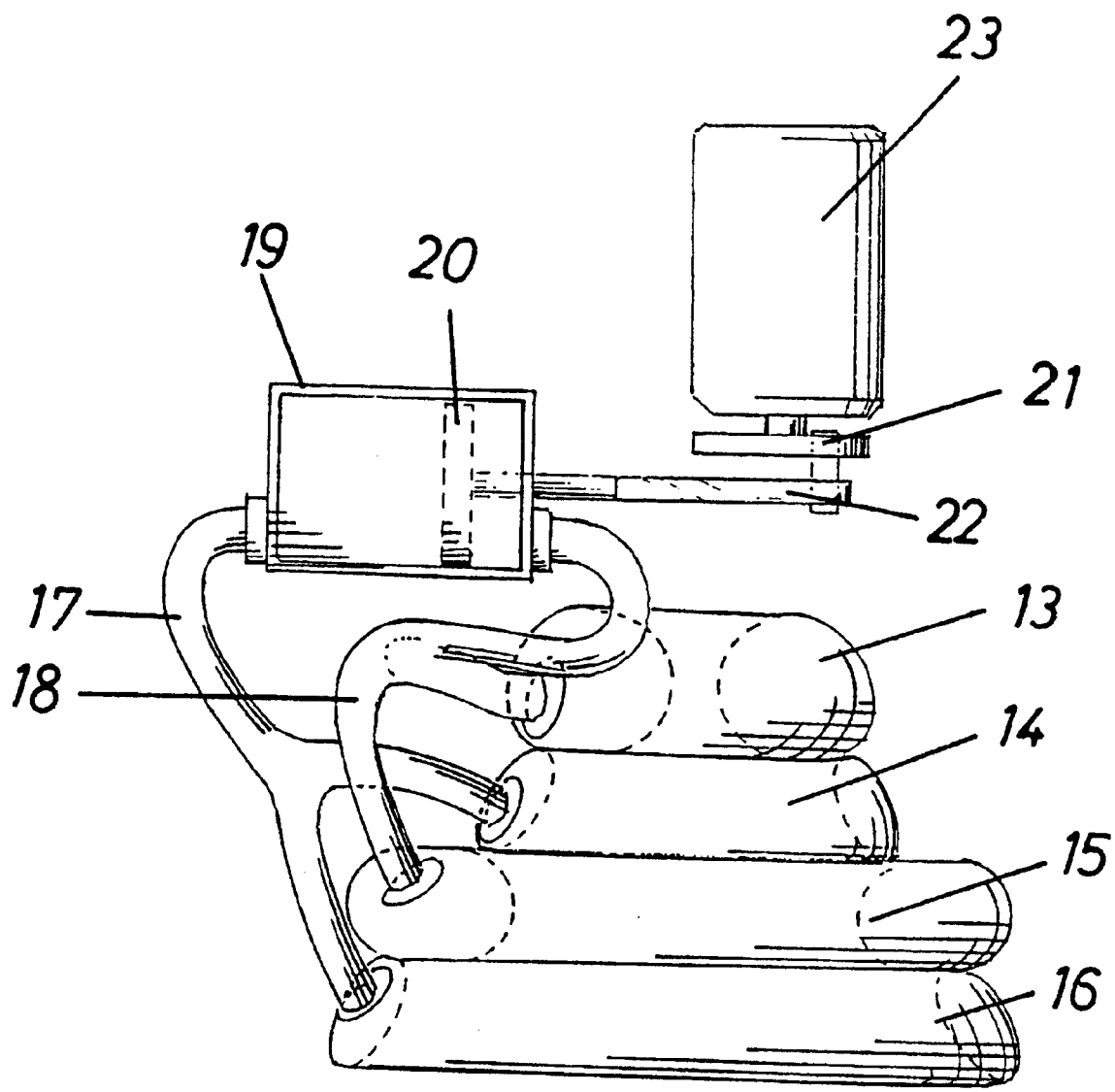
FIG. 3 shows a side view of a breast cup according to another embodiment of the invention.

FIG. 3 shows an embodiment of the breast cup having annular stimulating members 13–16 instead of rows of cells 6 and 12 as shown in FIGS. 1 and 2. Every second ring 13–16 is connected by tubing 17, 18 to its respective end of a cylinder 19 with an alternating piston 20. The piston 20 is operated, e.g., by an electric motor 23 via an eccentric sheave 21 and a driving rod 22. When the piston 20 is moved to the left in FIG. 3, pressurized medium, e.g., compressed air, will be supplied to the rings 14 and 16 via the tube 17, and these rings will expand. When the piston 20 is moved to the right in FIG. 3, pressurized medium, e.g., air, will be supplied to the rings 13 and 15 so that these expand, at the same time as the pressure in the rings 14 and 16 is relieved. This thus generates a pulsating wave towards the nipple. The frequency can be adjusted by altering the rotation speed of the motor 23. The part of the breast cup which is at the actual nipple is connected to a vacuum source in the same way as in the embodiments shown in FIGS. 1 and 2.

Amended Sheet

Figure 4:
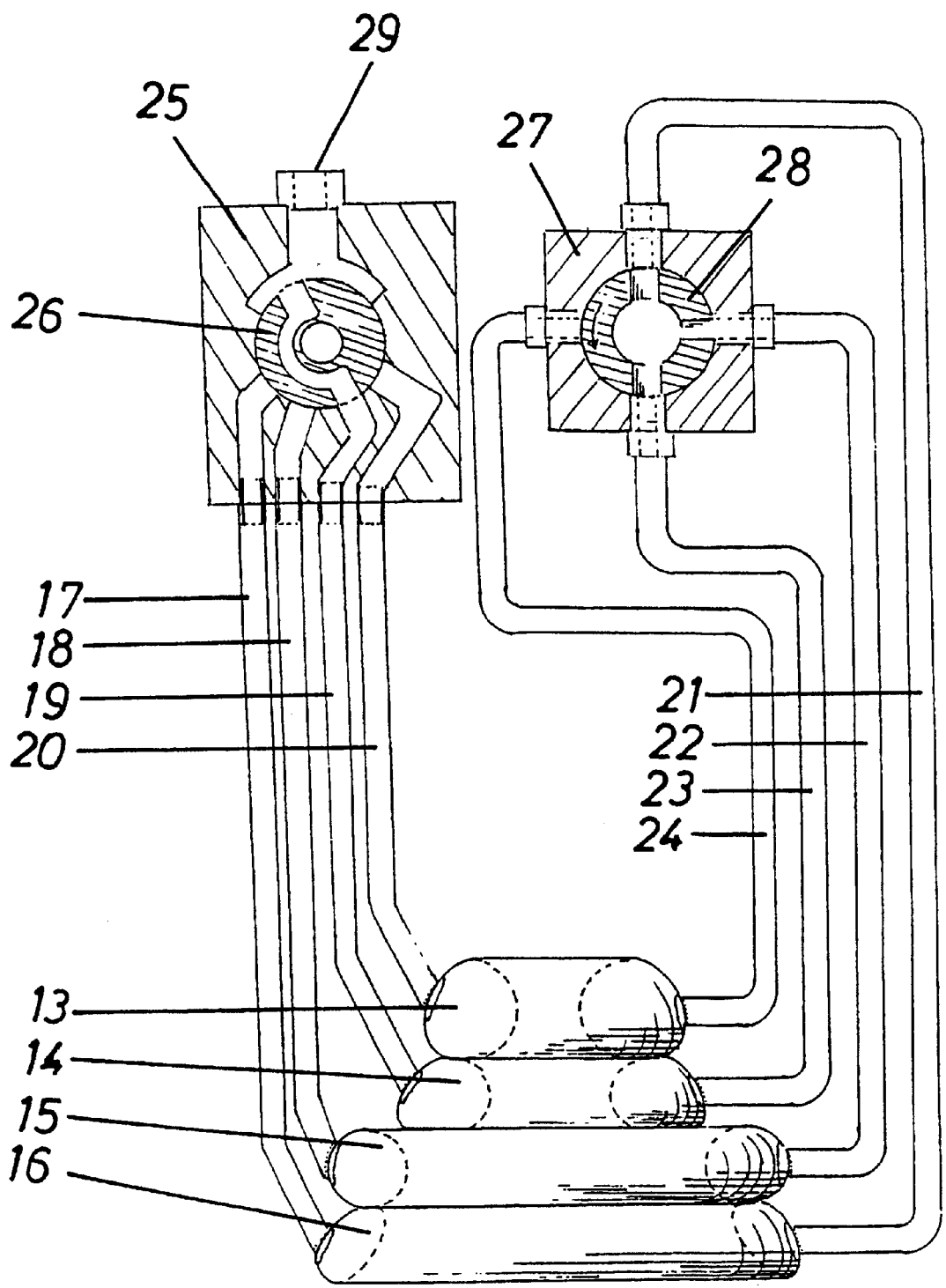
FIG. 4 shows a breast cup according to a third embodiment of the invention.

FIG. 4 shows a variant of the embodiment shown in FIG. 3. Here, the breast cup consists of a total of four rings 13–16, which are connected to one another by a control valve 25 for supply of pressurized medium via tubing 17–20, and a control valve 27 for relieving the pressure via tubing 21–24. Both valves 25 and 27 have a rotating valve member 26 and 28 with one or more through-going channels, for opening or closing the pressure supply or relief in the various rings 13–16. The supply valve 25 is supplied with pressurized medium, e.g., compressed air, via the inlet 29. The rotating valve member 26 is rotated to allow communication with one of the tubes 17–19, e.g., the tube 17. The pressurized medium is fed from the tube 17 into the ring 16, so that this expands. Then the valve element 26 is turned one more step, so that the pressurised medium is supplied via the pipe 18 to the next ring 15, so that this expands. The sequence continues thus so that the rings 16–13 are supplied with pressurized medium successively. At the same time, the valve element 28 of the relief valve 27 rotates, so that the pressure in the rings 13–16 is relieved successively. The pressurized medium can, e.g., be supplied from a compressor or similar. The frequency can be adjusted by altering the rotation speed of the valve elements 26 and 28, whilst the pressure can be adjusted by altering the pressure of the pressurized medium supplied.

The human breast milking apparatus according to the present invention is intended to be portable so that the energy supply to the pumps, compressors, motors and similar consists of batteries, preferably rechargeable batteries. The milking apparatus is intended to be connected to a receiving container, e.g., a bottle of the type generally used for feeding infants.

Furthermore, the breast cups according to all the embodiments of the invention can be connected to a suitable connector for connection to the receiving container, the vacuum source and so forth. The invention also comprises embodiments wherein the pressurized fluid is a liquid or a gas other than air.

What is claimed is:

1. A human breast milking apparatus including a breast cup, a collecting means connected to the breast cup, a source of vacuum, at least one source of pressurized fluid and a regulating device, the breast cup includes a generally conical portion and a generally cylindrical portion connected to that part of the conical portion which is smallest in diameter, characterized in that the breast cup in combination comprises:

a) a first stimulating member for stimulating a nipple, the first stimulating member consists of the generally cylindrical portion;

b) a second stimulating member for stimulating an area of the breast immediately around or in the immediate vicinity of the nipple, the second stimulating member is provided at or in the vicinity of that part of the conical portion which is smallest in diameter, wherein the second stimulating member consists of an annular chamber in the wall of the conical portion of the breast cup; and c) a third stimulating member for stimulating an area of the breast 2.5 to 3 cm from the base of the nipple, wherein the third stimulating member consists of a part of the conical portion which is 2.5 to 3 cm from the connection between the cylindrical portion and the conical portion, the third stimulating member consists of an annular chamber in the wall of the conical portion said first stimulating member, which consists of the generally cylindrical portion, is connected to the vacuum source which has adjustable pressure and frequency, the second stimulating member is connected to the pressurized fluid source having adjustable pressure and frequency, and the third stimulating member is connected to the pressurized fluid source having adjustable pressure and frequency, the frequency of the vacuum source and the pressurized fluid source being independently adjustable relative to one another, such that the pressure and the frequency of the second stimulating member are independently adjustable in relation to the pressure and the frequency of the third stimulating member, and that the second and third stimulating members are positioned for producing a pulsating wave from the area of the breast that is furthest from the nipple towards the part of the breast closest to the nipple.

2. The human breast milking apparatus according to claim 1, characterized in that the second stimulating member and the third stimulating member are connected to one or more pressure sources, having adjustable pressure and frequency.

3. The human breast milking apparatus according to claim 1 characterized in that the breast cup is made of a flexible, skin-friendly material.

4. The human breast milking apparatus according to claim 1, characterized in that the pressure of the first stimulating member can be adjusted within the range of 50 to 220 mm Hg, and the frequency can be adjusted with the range of 60 to 120 per minute.

5. The human breast milking apparatus according to claim 1 wherein the third stimulating member is a chamber in the form of one or more rows of cells interconnected by passages.

6. The human breast milking apparatus according to claim 1 wherein the pressure source is compressed air.

7. The human breast milking apparatus according to claim 2 wherein the one or more pressure sources are compressed air.

8. The human breast milking apparatus according to claim 1 wherein the breast cup is made of silicone.

* * * * *